United States Patent [19]

Lacy et al.

[11] Patent Number: 5,080,732

[45] Date of Patent: Jan. 14, 1992

[54] METHOD FOR DETERMINING THE RELATIVE HAZ TOUGHNESS OF STEEL

[75] Inventors: Lewis L. Lacy, The Woodlands, Tex.; Douglas P. Fairchild, Columbus, Ohio; Charles P. Royer, Houston, Tex.

[73] Assignee: Exxon Production Research Company, Houston, Tex.

[21] Appl. No.: 368,684

[22] Filed: Jun. 20, 1989

[51] Int. Cl.$^5$ .............................................. C21D 1/00
[52] U.S. Cl. ...................................... 148/127; 73/851
[58] Field of Search .................. 148/127, 128; 73/850, 73/760, 851, 844

[56] References Cited

U.S. PATENT DOCUMENTS 4,062,705 12/1977 Gondo et al. ........................ 148/127
4,142,713 3/1979 Nakasugi et al. ................... 148/127
4,864,867 9/1989 Manahan, Sr. ......................... 73/851

OTHER PUBLICATIONS

Fairchild, D. P., Royer, C. P., and Teisen, J. D., "Philosophy and Technique for Assessing HAZ Toughness of Structural Steels Prior to Steel Production", Seventh International Conference on Offshore Mechanics and Arctic Engineering, Houston, Texas, Feb. 7–12, 1988, pp. 247–255.

Bateson, P. H., Webster, S. E., and Walker, E. F., "Assessment of HAZ Toughness Using Small Scale Tests", Seventh International Conference on Offshore Mechanics and Arctic Engineering, Houston, Texas, Feb. 7–12, 1988, pp. 257–265.

Mackay, K., "CTOD Testing and Validation-State of the Art for Recent North Sea Projects", Seventh International Conference on Offshore Mechanics and Arctic Engineering, Houston, Texas, Feb. 7–12, 1990, pp. 267–273.

Kocak, M., Chen, L., Terlinde, G., Gnirss, G., and Schwalbe, K. H., "CTOD Testing of HAZ and Analysis of Pop-In Behavior", Seventh International Conference on Offshore Mechanics and Arctic Engineering, Houston, Texas, Feb. 7–12, 1990, pp. 297–304.

Hanus, F. E., "Influence of the Width of Weld Simulated Coarsed Grained Zones on the Charpy Transition Curve", Seventh International Conference on Offshore Mechanics and Arctic Engineering, Houston, Texas, Feb. 7–12, 1990, pp. 509–513.

Haze, T. and Aihara, S., "Influence of Toughness and Size of Local Brittle Zone on HAZ Toughness of HSLA Steels", Seventh International Conference on Offshore Mechanics and Arctic Engineering, Houston, Texas, Feb. 7–12, 1990, pp. 515–523.

*Primary Examiner*—S. Kastler
*Attorney, Agent, or Firm*—Exxon Production Research Company

[57] ABSTRACT

A method for determining the relative HAZ toughness of steel. The method comprises determining at least two thermal cycles of the steel for at least one weld heat input value and then simulating the HAZ that would result if the steel were actually welded in accordance with those thermal cycles. The steel is then fractured to determine various fracture properties, each of which may be used to determine the midpoint transition temperature associated with the fracture property used. The midpoint transition temperature is compared to a previously determined standard maximum midpoint transition temperature and if it is greater than the standard, the steel may have low HAZ toughness, but if it is less than the standard, the steel may have a high HAZ toughness.

11 Claims, 5 Drawing Sheets

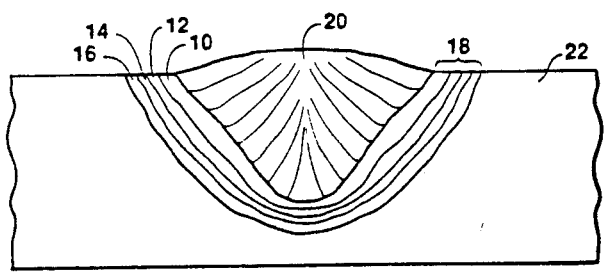
FIG. 1
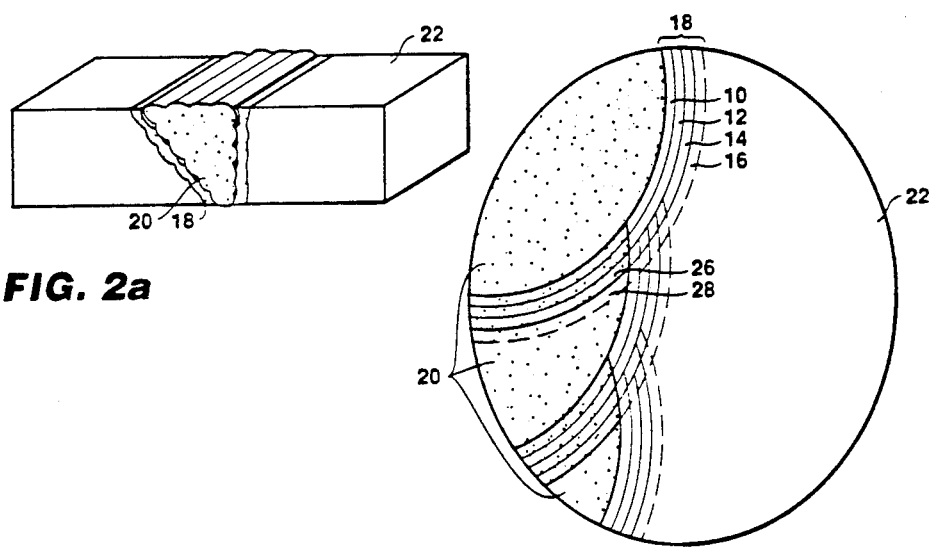
FIG. 2a
FIG. 2b
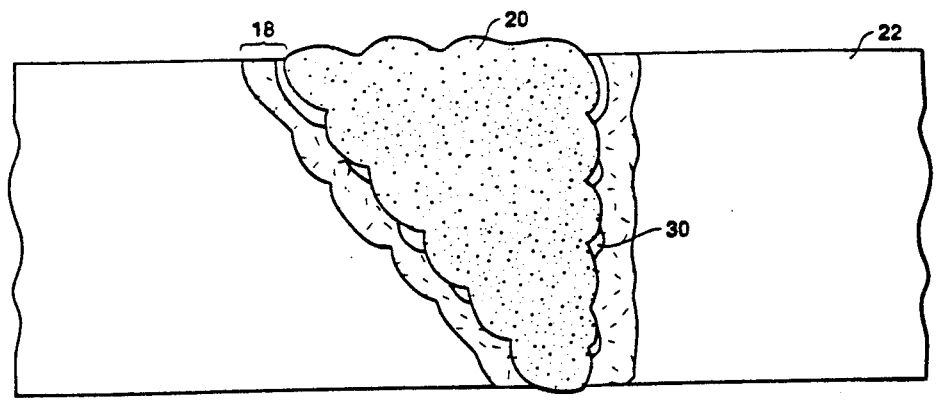
FIG. 3

METHOD FOR DETERMINING THE RELATIVE HAZ TOUGHNESS OF STEEL

FIELD OF THE INVENTION

This invention relates generally to the field of welded steels. More particularly, but not by way of limitation, the invention pertains to a method for determining the relative heat affected zone ("HAZ") toughness of steel.

BACKGROUND OF THE INVENTION

In offshore petroleum operations, platforms comprising a trussed steel framework, or jacket, secured to the sea floor and a deck mounted on top of the jacket are commonly used to drill for and produce oil and gas. Such an offshore structure will, by the nature of its fabrication, contain a considerable number of welded steel joints located in highly stressed regions. These welds may contain small zones of low fracture toughness, otherwise known as local brittle zones ("LBZs"), that may cause a local susceptibility to brittle fracturing. Industry is concerned that these LBZs may increase the probability of fracturing.

The process of welding produces HAZ in the steel adjacent to the weld metal which results from the intense heat associated with welding. FIGS. 1, 2A, 2B, and 3 are schematics of typical welds, each having a weld metal 20, base metal 22, and a HAZ 18. FIG. 1 illustrates the various regions of a typical single-pass bead-on-plate weld. As shown, with this type of weld the HAZ 18 is adjacent to the weld metal 20 and comprises coarse grain 10, fine-grain 12, intercritical 14, and subcritical 16 regions. In a typical multipass weld, as illustrated in FIG. 2B, the HAZ 18 of adjacent weld passes overlap and create additional coarse grain regions including the single thermal cycle region ("CGHAZ") 10, the two-thermal-cycle intercritically reheated region ("IRCG") 26, and the subcritically reheated region ("SRCG") 28. Low toughness behavior in the HAZ is caused by LBZs located within the HAZ. The coarse grain regions of the HAZ are a primary site for LBZs. LBZs are a direct result of welding thermal cycles that heat the base steel to a peak temperature near the melting temperature of the steel.

Although the structural significance of LBZs is not yet established in the industry, some steel users have elected to determine the HAZ toughness of candidate steels prior to purchase. Low toughness behavior is generally known to be greatest in the coarse grain regions of the HAZ. However, determining the HAZ toughness of a steel can be difficult because the LBZs in these coarse grain regions are small and discontinuous; performing quantitative toughness testing of these small regions is difficult. FIG. 3 is a schematic illustrating how LBZs 30, or low toughness coarse grain regions, might be positioned in an actual weld. LBZs are typically 0.25 to 0.5 mm thick and 1.0 to 5.0 mm high.

Various tests are commonly used in the industry to determine the HAZ toughness of various steels. One such test is the crack tip opening displacement test ("CTOD"). CTOD testing involves initiating and propagating a fatigue crack in a steel sample and subsequently testing that sample to final fracture. The resulting CTOD value represents the width of the fatigue crack tip blunting prior to failure, which characterizes the fracture toughness of the steel. CTOD values below 0.10 mm are generally considered to indicate low resistance to fracturing, or low toughness, and CTOD values above 0.25 mm are generally considered to indicate high resistance to fracturing, or high toughness. To evaluate the fracture toughness of the coarse grain zones having LBZs, the fatigue crack tip must terminate in the coarse grain region. As discussed above, these regions are small and therefore placement of the fatigue crack is difficult. Furthermore, waviness of the weld beads in the weld direction and fusion line waviness in the through thickness direction will create significant difficulties for locating the fatigue crack tip in the correct zone of interest. In addition, the fatigue crack, even if in the correct position within the HAZ, may deviate into the base or the weld metal.

Because of the problem with fatigue crack tip placement, various standards in the industry, such as the American Petroleum Institute Recommended Practice 2Z ("API RP 2Z") and the Engineering and Equipment Material Users Association Standard ("EEMUA 150") which are well known to those skilled in the art, provide that a minimum number of samples must show that the fatigue crack tip is in the coarse grain regions for a minimum percentage of the sample thickness in order to ensure the accuracy of test results. To make this determination, detailed metallographic studies must be performed on at least 30 to 60 weldment samples, and as a result, CTOD testing can take as long as six months or more to complete and can be very expensive.

The present invention is aimed at alleviating the above described problems and providing a practical method for determining the relative HAZ toughness of steel prior to purchase. It is a further aim of the invention to reduce testing time and cost so that the influence of steel chemistry and manufacturing procedures can be economically evaluated to improve the HAZ toughness.

BRIEF DESCRIPTION OF THE DRAWINGS

The advantages of the present invention will be better understood by referring to the following detailed description and the attached drawings in which:

FIG. 1 illustrates the various HAZ regions of a single-pass, bead-on-plate weld.

FIG. 2A illustrates a multipass weld.

FIG. 2B illustrates the various HAZ regions of a multipass weld.

SUMMARY OF THE INVENTION

Figure 4:
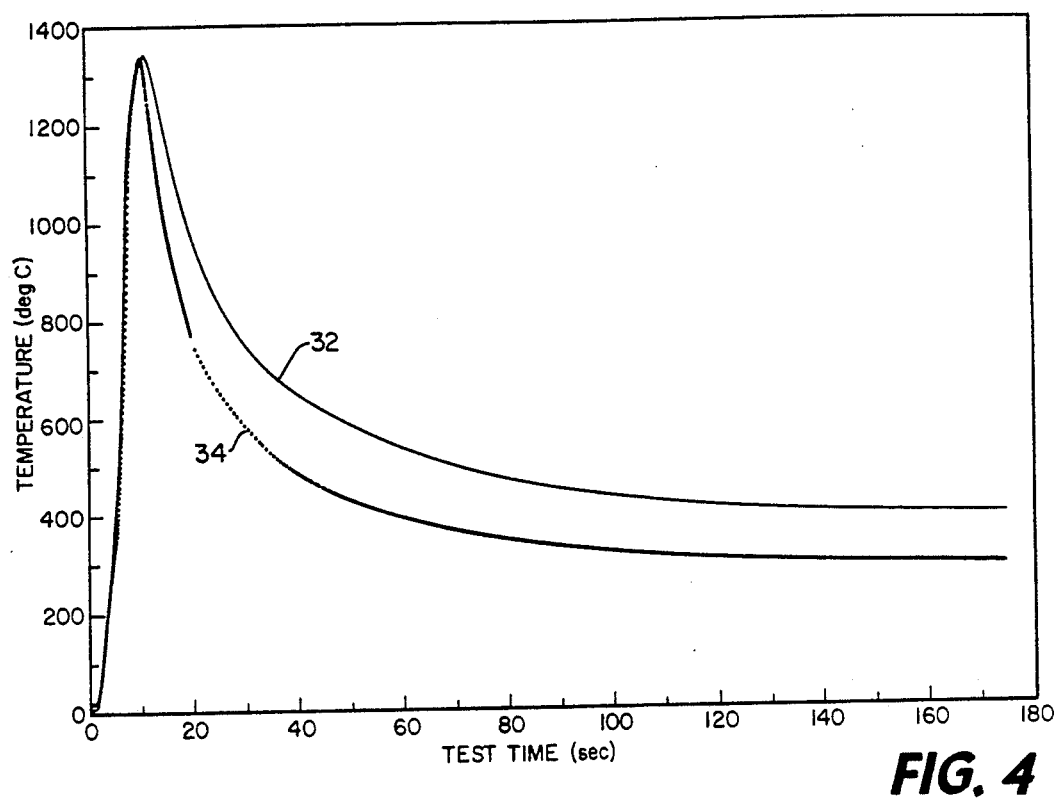
FIG. 4 illustrates the weld thermal cycles at weld heat input values of 3 and 5 kJ/mm used to simulate a CGHAZ.

The present invention is a method for determining the relative HAZ toughness of steel. Upon welding, steel will have a HAZ as a result of welding thermal cycles which are related to various weld heat input values. Midpoint transition temperatures associated with four fracture properties, including total fracture energy, initiation energy, propagation energy, and dynamic fracture toughness, are related to each of the welding thermal cycles. The steel being tested is within a range of steels having a previously determined standard maximum midpoint transition temperature and previously determined standard minimum CTOD values.

The first step of the method is determining at least two thermal cycles of the steel for at least one weld heat input value. The steel is then heated and cooled in accordance with these thermal cycles to simulate the HAZ. The total fracture energy, the initiation energy, the propagation energy, or the dynamic fracture toughness necessary to fracture the steel is then determined for a plurality of temperatures and plotted as a function of temperature. The midpoint transition temperature of the thermal cycle is determined from the plot and compared to the previously determined standard maximum midpoint transition temperature. If the midpoint transition temperature is greater than the standard maximum midpoint transition temperature, then the steel may have a low toughness, but if the midpoint transition temperature is less than the standard maximum midpoint transition temperature, then the steel may have a high toughness.

The standard maximum midpoint transition temperature for the range of steels is determined by correlating the midpoint transition temperature for each steel, as determined in the manner described above, with the previously determined standard minimum CTOD value of each steel.

DETAILED DESCRIPTION OF THE PREFERRED EMBODIMENTS

When an offshore platform is constructed, certain high-strength steels with typical minimum yield strengths of approximately 50 ksi and minimum tensile strengths of approximately 70 ksi are tested to verify that their toughness, or their ability to withstand fracturing, is adequate. With welded steels, high toughness values are necessary in the base metal, the weld metal, and the weld HAZ. The base-metal toughness is generally adequate, however, as previously discussed, the HAZ toughness is a subject of industry wide concern.

The present invention is a method for determining the relative HAZ toughness of steel. It will be understood that although the invention will be described in connection with determining the relative HAZ toughness of steel used in the construction of offshore platforms, the invention may also be used to determine the HAZ toughness of other types of steels such as steels used to construct other structures pressure vessels and pipelines. Accordingly, all such uses are intended to be included within the scope of the invention.

The first step in determining the relative HAZ toughness of a steel is to determine at least two thermal cycles of the steel for at least one weld heat input value. Generally, a thermal cycle is the time dependent temperature of the HAZ under a specific set of welding conditions. Preferably, the two thermal cycles determined are the thermal cycle related to the CGHAZ and the thermal cycle related to the IRCG. LBZs may develop in either the CGHAZ or the IRCG, or in both. Accordingly, because LBZs cause low toughness behavior, the thermal cycles of both should be determined for the desired weld heat input value in order to obtain an accurate measurement of the relative HAZ toughness of the steel. Third and fourth welding thermal cycles can also be measured. However, these cycles, which result from third and fourth welding passes, do not normally decrease the HAZ toughness of the steel and are therefore not usually necessary to the determination of the relative HAZ toughness. Once the thermal cycles are determined, they will be used to simulate the HAZ, including the CGHAZ and the IRCG, which would result if the steel was actually welded in accordance with those thermal cycles.

The thermal cycles are determined using techniques known to those skilled in the art and are described by plotting the temperature during welding of the CGHAZ and the IRCG as a function of time. One such technique uses thermocouples, which are placed in holes in a steel sample at various distances from the fusion line to be found upon welding, to measure the temperature of the HAZ as the welding rod traverses the sample. Several welding variables including the weld geometry, the plate thickness, the weld heat input, the peak temperatures, and the preheat temperature are important to the determination of the welding thermal cycles. Generally, the weld heat input is the measure of the amount of energy deposited in a weld per unit of weld length. The peak temperature is the highest temperature of the welding thermal cycle. The preheat temperature is the temperature to which the base metal is heated before welding to avoid hydrogen or cold cracking. These variables depend on the type of welding desired and the type of construction performed.

Figure 5:
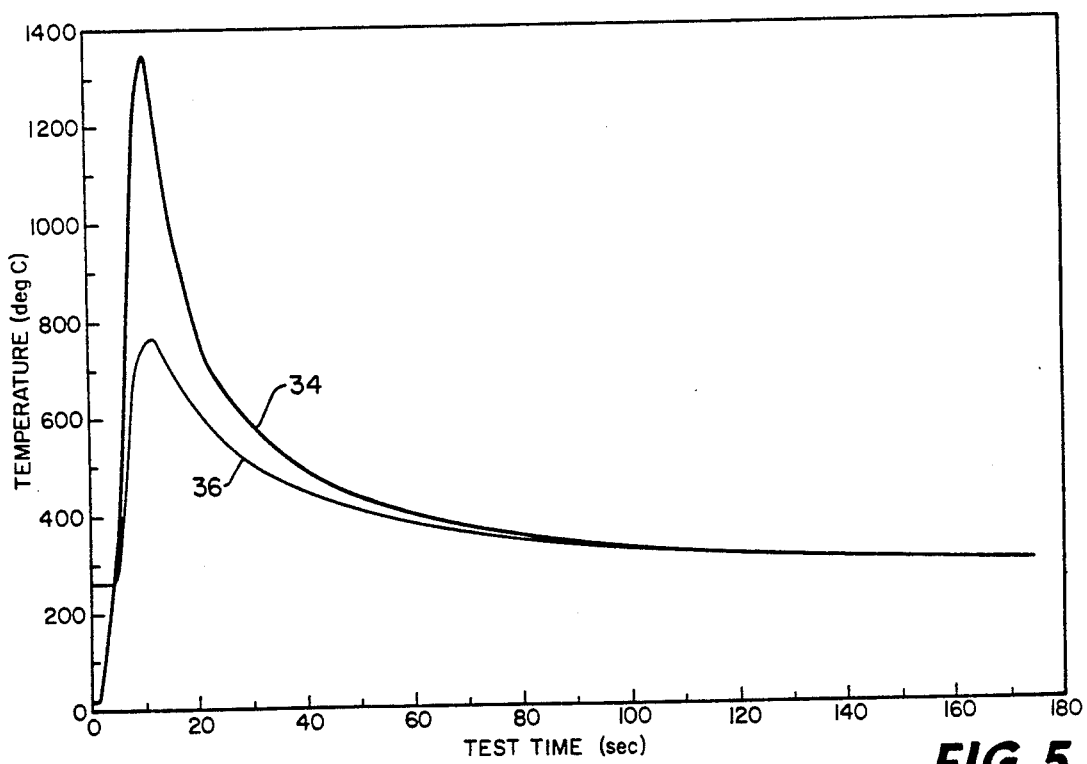
FIG. 5 illustrates the first and second thermal cycles for a weld heat input value of 3/3 kJ/mm used to simulate the IRCG.

FIGS. 4 and 5 illustrate weld thermal cycle data plots which were determined for an offshore platform steel. FIG. 4 compares the weld thermal cycles used to simulate the CGHAZ at weld heat inputs of 3 and 5 kJ/mm. The thermal cycle for the weld heat input of 5 kJ/mm is illustrated by the upper curve 32, and the thermal cycle for the weld heat input of 3 kJ/mm is illustrated by the lower curve 34. These thermal cycles were determined for bead-on-plate welds with plate thicknesses of 2 inches or greater and a peak temperature of 1350° C. FIG. 5 compares the two weld thermal cycles used to simulate the CGHAZ and the IRCG at a weld heat input of 3 kJ/mm. The thermal cycle used to simulate the CGHAZ is identical to that illustrated in FIG. 4 as the lower curve 34 for a weld heat input of 3 kJ/mm. The same weld geometry and plate thickness were used for the measurement of both thermal cycles. The second thermal cycle is illustrated as FIG. 5 as the lower curve 36. The peak temperature of the second thermal cycle related to the IRCG is 770° C., and the weld interpass temperature, which is the starting temperature for the second welding pass, is 250° C. The thermal cycles illustrated in FIGS. 4 and 5 were determined for steel which was preheated to approximately 93° C. to avoid hydrogen or cold cracking. This represents a typical preheat temperature for platform construction.

In a preferred embodiment of the present invention, plots of the measured temperature versus time data for each thermal cycle are compared with model predictions of that thermal cycle for varying peak temperatures in order to ensure the accuracy of each thermal cycle. Various equations, which are well known to those skilled in the art, may be used to make such model predictions. As described below, to further ensure the accuracy of the thermal cycles, the cooling time of each thermal cycle as a function of the weld heat input is also compared to model predictions.

Figure 6:
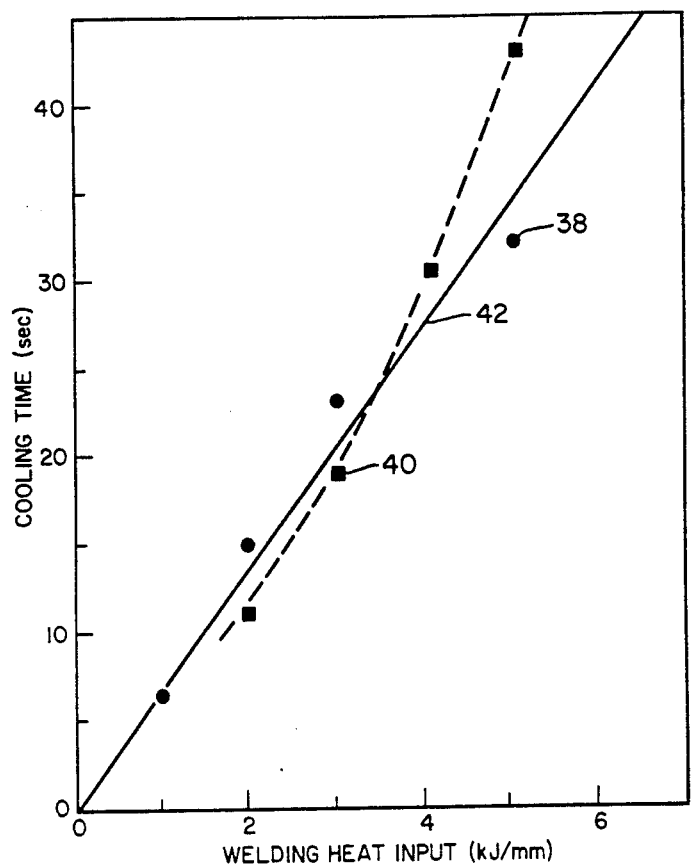
FIG. 6 illustrates the measured cooling times for two plate thicknesses and the calculated cooling times for a thick plate model plotted as a function of weld heat input values.

The cooling time, between 800° C. and 500° C., may influence the metallurgical microstructure of the HAZ and consequently the HAZ toughness. FIG. 6 illustrates such a comparison. The measured cooling times between 800° C. and 500° C. are plotted as a function of weld heat inputs for both one and two inch thick steel plates. The data 40 for the one inch thick plates are marked by squares, while the data 38 for the two inch thick plate are marked by circles. The calculated cooling time for a thick plate model is also plotted as a function of weld heat input and is illustrated as line 42. As shown, for weld heat inputs less than approximately 3.5 kJ/mm, there is reasonable agreement between the thick plate model and the data for both the one and two-inch thick plates. However, for heat inputs higher than 3.5 kJ/mm, the data 40 for the one-inch thick plate has a significantly longer cooling time than the cooling time for the thick plate model 42. Accordingly, to ensure the accuracy of the thermal cycles and therefore accurately simulate the HAZ for the desired welding parameters, the cooling time should be consistent with plate thickness and cooling times of interest. For example, referring again to FIG. 6, the correct cooling time for a one-inch steel plate at a 5 kJ/mm heat input would be approximately 43 seconds, whereas the cooling time for the two-inch steel plate would be approximately 31 seconds.

Once the weld thermal cycles for the desired welding parameters are determined, the steel samples are heated and cooled in accordance with the measured thermal cycles to simulate the HAZ, including the CGHAZ and the IRCG. A weld thermal cycle simulator can be used to simulate these regions. One such simulator is a Gleeble 1500 which is commercially available and well known in the industry. It should be noted that any method for heating and subsequently cooling the steel in accordance with the desired thermal cycles may be used to simulate the HAZ, provided simulation accuracy, as further described below, is controlled. The thermal cycles determined are converted into Gleeble computer software to control the simulation. The sample size and shape, alloy composition, and width of the simulation zone can be varied to meet test requirements.

As previously discussed, key welding parameters affecting the HAZ thermal cycle include peak temperature, welding heat input, preheat, and steel-plate thickness. In a preferred embodiment, the following welding parameters were used to simulate the HAZs, including the CGHAZs and the IRCGs, of offshore platform steels. The peak welding temperatures used when simulating the CGHAZ and the IRCG were between 1200° C. and 1450° C., preferably 1350° C., for the CGHAZ, and between 680° C. and 800° C., preferably 770° C., for the IRCG. These peak temperatures were selected to yield HAZs having the worst, or lowest, toughness values while ensuring that the temperatures were not so high as to render the thermocouples inoperative. Welding heat input values of 1.5, 3, and 5 kJ/mm were selected to correspond to a wide range of welding heats commonly used in platform construction and specified in API RP 2Z. The plate thickness was selected as two inches or greater to represent steel plates used in offshore structures. For a given weld heat input value, a minimum of 24 samples were simulated, each having a uniform simulated CGHAZ or IRCG of approximately 5 to 8 mm. Twelve samples were simulated to represent the CGHAZ and 12 samples were simulated to represent the IRCG. The large simulated HAZ alleviates the fatigue crack placement problem arising with actual welds which have a much smaller HAZ (typically 3 to 4 mm wide) with potentially smaller and discontinuous LBZs.

To use the Gleeble simulator, the steel sample is clamped between two water-cooled copper jaws and heated by low-voltage AC power supplied by an AC power controller. In a preferred embodiment, the distance between the copper jaws should be set at 16 mm to ensure uniform simulation zones of about 5 to 8 mm width. The jaw spacing selected should be wide enough to yield wide simulation zones and narrow enough to ensure that the cooling characteristics of the thermal cycle are accurate. If the spacing is too wide, the sample will not cool fast enough.

The temperature of each sample is measured approximately 120 times per second using a thermocouple spot-welded to the sample. The measured Gleeble sample temperature is compared to a temperature that was preprogrammed into the simulator. Both the sample temperature and the program temperature are measured and recorded 30 times per second using a data acquisition system which is automatically triggered by the Gleeble simulator and is programmed to plot key variables on a display monitor and print a test report at the end of each simulation. The report summarizes all major variables and test plots and serves as documentation and quality control for each HAZ simulation. Accuracy is controlled by rejecting any sample where the measured peak temperature and the measured cooling temperature differ by ±15° C. from the preprogrammed welding temperatures.

In a preferred embodiment, the sample hardness and microstructure are studied, as described below, to ensure that the simulated HAZs accurately reflect the microstructure encountered in actual welds. As is well known to those skilled in the art, HAZ hardness can be determined using Vickers microhardness measurements and can be correlated with other hardness numbers and the tensile strengths of steels. By measuring and comparing Vickers microhardness measurements for the simulated sample with those measurements for the corresponding actual welded plates, the uniformity and the accuracy of the simulated zone can be established. To further ensure the uniformity and accuracy of the simulated zone, the grain size and microstructural components of the simulated sample can be compared to the grain size and microstructural components of the corresponding actual weld using optical, scanning electron, and transmission electron microscopy.

Once the HAZ, including the CGHAZ and the IRCG, has been simulated for the desired weld parameters, the next step in determining the HAZ toughness of the steel is to determine the total fracture energies necessary to fracture the steel for a plurality of testing temperatures. These total fracture energy values are determined by performing Instrumented Precracked Charpy Tests ("IPC") on each sample. It should be noted that any of three other fracture properties, including the initiation energy, the propagation energy, and the dynamic fracture toughness may be determined instead of, or in addition to, the total fracture energy to determine the HAZ toughness of steel. Generally, the total fracture energy is the total energy required to fracture the sample at a given temperature. Further, the initiation energy is the energy required to initiate fracturing, and the propagation energy is the energy required to propagate the fracture. The following will describe IPC testing with reference to determining the total fracture energy necessary to fracture the steel rather than to determining any of the other three fracturing properties. However, the method is not intended to be limited to determination of the total fracture energy as any of the other three fracture properties may be used.

IPC testing was developed for the nuclear industry to determine dynamic fracture toughness of reactor steels used in pressure containment because of the potential for steel embrittlement caused by neutron bombardment. IPC tests have also been used by the aircraft and space industries to develop fracture-resistant materials subjected to cold or cryogenic temperatures. IPC tests use a fatigue-cracked sample and, as described below, are therefore more sensitive than standard Charpy tests which use a V-notched sample. The V-notch is blunt, and the resulting stress concentration is lower and broader than that resulting from a fatigue crack. Consequently, fatigue-cracked samples are more likely to detect local embrittlement, such as LBZs, than are those with V-notches. IPC testing offers several additional advantages to Charpy V-notch testing including means for determining other fracture properties such as fracture initiation and propagation energies and means for measuring dynamic fracture toughness. IPC testing also provides advantages over CTOD testing including reductions in data scattering, sample size, testing time, and cost.

In a preferred embodiment, the total fracture energies necessary to fracture offshore platform steels are determined by testing a minimum of 12 samples of the same steel, each sample having the same simulated HAZs for a plurality of IPC test temperatures in the range of −150° F. to 300° F. It may be necessary to modify this temperature range for other types of steels.

To perform the IPC test, each sample is preferably machined to Charpy size (10×10×55 mm) and contains a narrow machined notch, preferably approximately 0.005 inches, that is used to initiate a fatigue precrack. This fatigue precrack can be produced by an automatic, displacement-controlled precracker in accordance with the procedures specified in British Standard BS5762, which is generally consistent with the American Society for Testing and Material ("ASTM") Standard E399. Both of these standards apply to precracking samples used in fracture toughness testing. The actual fatigue-crack depth should be approximately 5 mm and the three-point bending equipment should use initial maximum loads of approximately 800 pounds and minimum loads of approximately 250 pounds. These parameters yield fatigue cracks which are coplanar and show no evidence of dimpling or overstressing. Furthermore, these parameters yield good quality fatigue cracks on HAZ simulated samples with typically 45,000 to 60,000 fatigue cycles and the stress intensity factor specified in BS 5762 is not exceeded during the final crack growth of 1 or 2 mm.

Figure 7:
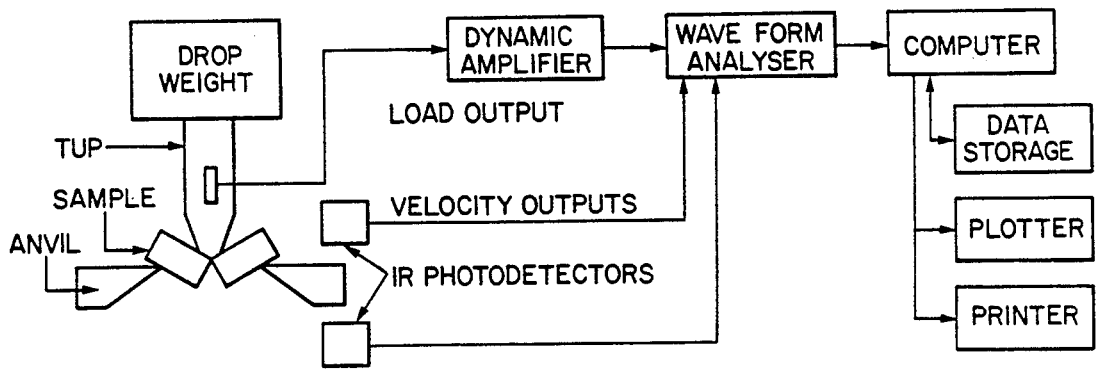
FIG. 7 illustrates the Instrumented Precracked Charpy equipment used in a preferred embodiment of the present invention.

After each steel sample has been precracked, the IPC equipment is used to fracture the steel sample for a plurality of testing temperatures in order to subsequently determine the total fracture energies for those temperatures. A schematic of the equipment used is shown in FIG. 7. An instrumented tup, having a drop weight and containing several strain gauges, strikes the test sample, which is restrained on two edges by an anvil designed to ASTM standards. The tup force sensor is calibrated to an accuracy of approximately ±7 pounds for loads up to approximately 10,000 pounds using a calibrated load cell.

The load required to break the sample is determined by amplifying the strain gauge signal using a wide-band (approximately 125 kHZ) and bridge-balanced dynamic amplifier and digitally recording the signal with an HP wave-form analyzer. The wave-form analyzer records 16,384 readings with 12-bit resolution using sample intervals of 0.25 to 10 microseconds, where a 1 microsecond sample interval is typical. A Hewlett Packard Vectra computer automatically sets up the wave-form analyzer parameters and selects optimum settings based on drop parameters such as test temperature, impact velocity, amplifier gain, and amplifier band width. Another key parameter is the fatigue-crack depth which is measured at five locations on each sample to an accuracy of ±0.001 inch. The average fatigue-crack depth is used to calculate and plot the measured fracture energy per unit area created during fracture testing. This energy is referred to as the normalized fracture energy.

When the tup of the falling drop weight impacts a sample, the energy delivered to the sample will be time dependent. The force measured on the tup ("F(t)") will be used to calculate this energy. The energy delivered by the falling weight is calculated with the following equations:

$$E(t) = V_o I_o(t) + g I_1(t) - I_o^2(t)/2M \qquad \text{Eq. (1)}$$

where
$E(t)$ = the total fracture energy, the initiation energy, or the propagation energy, depending on the time;
$V_o$ = the initial impact velocity;
$M$ = the mass of the falling drop weight;
$g$ = the acceleration due to gravity; and $$I_o = \int_0^t F(t)dt = \text{impulse;} \qquad \text{Eq. (2)}$$

and $$I_1 = \int_0^t t F(t)dt = \text{first moment of impulse.} \qquad \text{Eq. (3)}$$

The derivation of these equations and the equation for determining the dynamic fracture toughness can be found in Appendix A.

In addition to determining the load required to break the steel sample, the velocity of the tup is simultaneously determined at the moment of impact and after fracturing the sample by measuring the transit time of a metal flag attached to the falling weight and detected by two infrared photodetectors. Two independent measurements of the total fracture energy can therefore be calculated, allowing for enhanced confidence in the data recorded.

The total fracture energy can be determined in this manner from the following equation.

$$E = M(V_o^2 - V_f^2)/2 + MgX_d \qquad \text{Eq. (4)}$$

where
E = total fracture energy;
M = mass of the falling drop weight;
$V_o$ = velocity of the falling tup at the point of impact;
$V_1$ = velocity of the falling tup after the sample has fractured.
g = acceleration due to gravity,
$X_d$ = distance between photodetectors.

The derivation of this equation can be found in Appendix A.

To ensure reliable and accurate results, the drop weight tests are performed on calibrated Charpy samples of steel which may be obtained from the U.S. Army Materials Testing Laboratory. Calibrated aluminum samples may be used to check the accuracy of the breaking load. Typical drop parameters that provide reliable and reproducible results are a drop weight of 500 lbs. and a drop height of six inches.

A standard Charpy pendulum device, rather than the IPC equipment described above, could be used to determine the total fracture energies of the precracked samples. However, a disadvantage of the standard Charpy pendulum device is its inability to determine the fracture initiation and propagation energies and its lack of sensitivity and accuracy for measuring total fracture energies less than 5 ft*lb. Another disadvantage to using a standard Charpy pendulum device is that there are uncertainties in measurements which are associated with oscillations caused by inertial effects. The Charpy pendulum device is a low mass but high velocity device which increases the probability of having inertial effects. The IPC equipment is a higher mass, lower velocity device which yields better quality data having less data scatter than that resulting from the use of the Charpy pendulum device.

Figure 8:
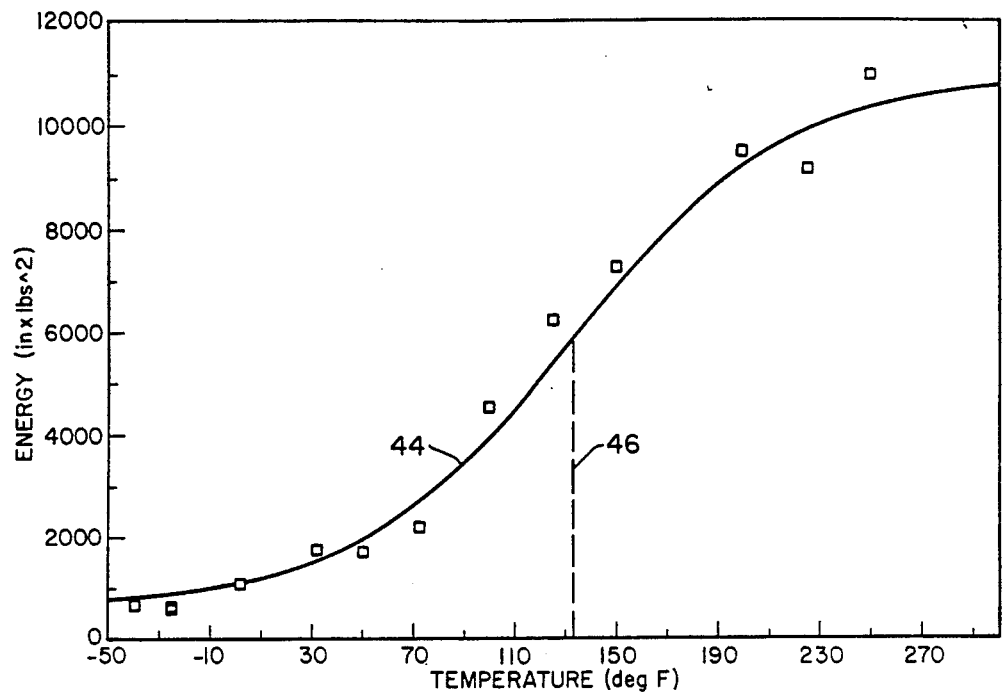
FIG. 8 illustrates the total fracture energy of a steel at a weld heat input value of 5/5 kJ/mm plotted as a function of temperature.

The total fracture energies determined from the results of the IPC tests are then plotted as a function of the test temperatures. FIG. 8 illustrates such a plot, with the data fitted as curve 44. With this particular steel, at temperatures less than approximately 30° F., the total fracture energy is small (less than approximately 500 in*lb/in$^2$) and approximately constant. This lower-bound energy is defined as the lower shelf and represents cleavage or brittle fracturing. It is often associated with linear elastic fracture mechanics. At test temperatures greater than approximately 200° F., the total fracture energy is large (greater than 9000 in*lb/in$^2$) and approximately constant. This is referred to as the upper shelf. Fracturing near the upper shelf region constitutes ductile fracture propagation and involves elongation or distortion of the fracture faces with distinct shear lips. Data in the transition zone are sometimes referred to as mixed-mode fracturing and may involve both brittle and ductile fracture growth on different parts of the fracture face.

A midpoint transition temperature can be determined from each total fracture energy versus test temperature plot and is the temperature at which the total fracture energy is at a midpoint. To accurately determine the midpoint transition temperature, at least two samples must be IPC tested at the upper shelf; at least one sample must be IPC tested at the lower shelf; and a minimum of six to eight samples must be IPC tested in the transition zone. As illustrated by the dashed line 46 in FIG. 8, the midpoint transition temperature of this particular curve is approximately equal to 132.6° F. To determine the midpoint transition temperature, the data must first be fit to a smooth "S" shaped curve by least squares regression. The equation used to fit the data is in the following form:

$$E = A + B * TANH\ [(T - T_o)/C]$$

where E is any of the fracture properties of interest (initiation energy, propagation energy, total fracture energy or dynamic fracture toughness) and A, B, C and $T_o$ are regression parameters. The upper shelf energy is equal to A + B, the lower shelf energy is equal to A − B, and $T_o$ is the midpoint transition temperature. The width of the transition temperature zone is equal to 2C. The optimum set of parameters for fitting the data are determined by mathematically linearizing the fracture properties in the transition temperature zone and then using least square linear regression. Statistical curve fitting parameters, such as the standard deviation, of the fit over the entire temperature range and over the transition temperature range are determined to specify the accuracy of the curve fit and the amount of data scattering. Because temperature is an important parameter in these measurements, it is essential that the sample temperature be accurately measured within ±1° F. and controlled in regulated and stirred temperature baths.

Figure 9:
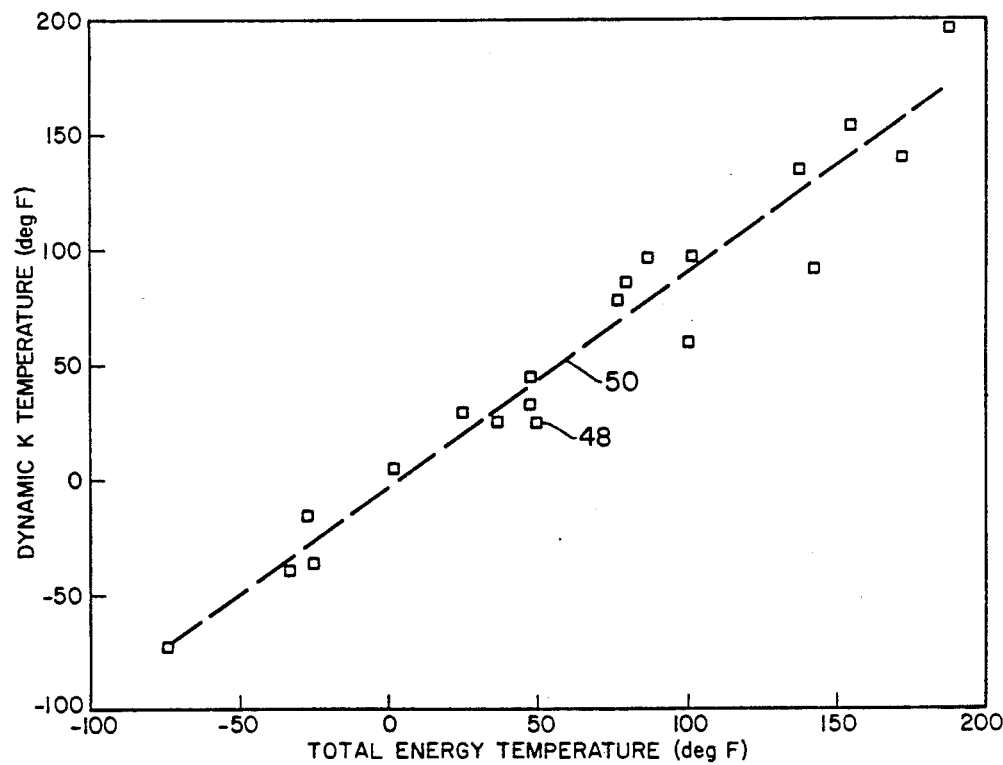
FIG. 9 illustrates the midpoint transition temperatures for dynamic fracture toughness plotted as a function of the midpoint transition temperatures for total fracture energy.

It should be reemphasized that any of the other three fracture properties, including the initiation energy, propagation energy and dynamic fracture toughness may be determined from the IPC test and plotted as a function of IPC test temperatures. These plots will generally show behavior, or curves, similar to that of the total fracture energy plots. The midpoint transition temperatures can then be determined from any of these plots. Each plot will yield approximately the same midpoint transition temperature. FIG. 9 is a plot of the midpoint transition temperatures associated with the dynamic fracture measurements versus the midpoint transition temperatures associated with the total energy. Dashed line 50 in FIG. 9 indicates that the midpoint transition temperatures of these two fracture properties are related over a wide temperature range, thereby verifying that the midpoint transition temperature can be determined from any one of the plots of the four fracture properties versus IPC test temperature. This correlation between midpoint transition temperatures will apply for base metals with yield strengths of 50 ksi and simulated HAZ with yield strength between 70 to 100 ksi.

After the total fracture energy, initiation energy propagation energy, or dynamic fracture toughness data is fit to a smooth "S" shaped curve and the midpoint transition temperature is determined, the midpoint transition temperature is compared to a previously determined standard maximum midpoint transition temperature for the range of steels being tested. If the midpoint transition temperature is greater than the standard maximum midpoint transition temperature, then that steel may have a low toughness, or a low resistance to fracturing, but if the midpoint transition temperature is less than the standard maximum midpoint transition temperature, then that steel may have a high toughness, or a high resistance to fracturing. The range of steels being tested is determined by minimum yield strength, tensile strength, plate thickness, steel chemistry, manufacturing techniques and manufacturing variables. For example, the standard maximum midpoint transition temperature is approximately 95° F. for offshore platform steels having a specified minimum yield strength of 50 ksi, a typical tensile strength of 70-80 ksi, and plate thickness of 2 to 3.5 inches with varying steel chemistries, manufacturing techniques and manufacturing variables.

In a preferred embodiment, to determine the standard maximum midpoint transition temperature for a range of offshore platform steels, the midpoint transition temperatures of each steel are determined, as described above, for welding heats of 3, 5, and 3/3, and 5/5 kJ/mm. Double pass welding cycles used to simulate the IRCG are specified as 3/3 or 5/5 kJ/mm. Consequently, for a given steel, four values of the midpoint transition temperature are determined, and the maximum value of the four will represent the worst case for that steel. The maximum midpoint transition temperatures for each steel are correlated with previously determined standard minimum CTOD values of each steel to derive the standard maximum midpoint transition temperature.

Maximum midpoint transition temperature values for various welding conditions are compared in Table 1 with prequalification CTOD data, performed similar to API RP 2Z. This method for determining the minimum CTOD values for welded steel is well known to those skilled in the art. A steel does not pass API's prequalification tests if there are two or more CTOD values less than 0.25 mm. As previously described, steels with CTOD values less than 0.10 mm indicate that the steel may have low HAZ toughness. The minimum CTOD values shown in Table 1 represent CTOD data on 10 or more samples. The percent of samples with CTOD values equal to or less than 0.1 mm are also shown.

TABLE 1

Comparison of IPC Midpoint Transition Temperatures Prequalification CTOD Test Results

| Platform Steel ("PS") Code | Maximum Midpoint Temperature (°F.) | Minimum CTOD (mm) | Percent CTOD Below 0.1 mm |
|---|---|---|---|
| PS1 | 65 | 0.29 | 0 |
| PS2 | 76 | 0.26 | 0 |
| PS3 | 85 | 0.29 | 0 |
| PS4 | 89 | 0.32 | 0 |
| PS5 | 138 | 0.024 | 20 |
| PS6 | 154 | 0.016 | 17 |
| PS7 | 178 | 0.014 | 33 |

Table 1 indicates that LBZ susceptible steels, or steels having CTOD values less than 0.1 mm (i.e. PS5, PS6 and PS7), have maximum midpoint transition temperatures greater than 130° F., and all prequalified steels, or steels having CTOD values greater than 0.25 mm, (i.e. PS1, PS2, PS3, and PS4) have maximum midpoint transition temperatures lower than 89° F. Therefore, the standard maximum midpoint transition temperature for the range of steel tested is approximately between 89° F. and 130° F.

Figure 10:
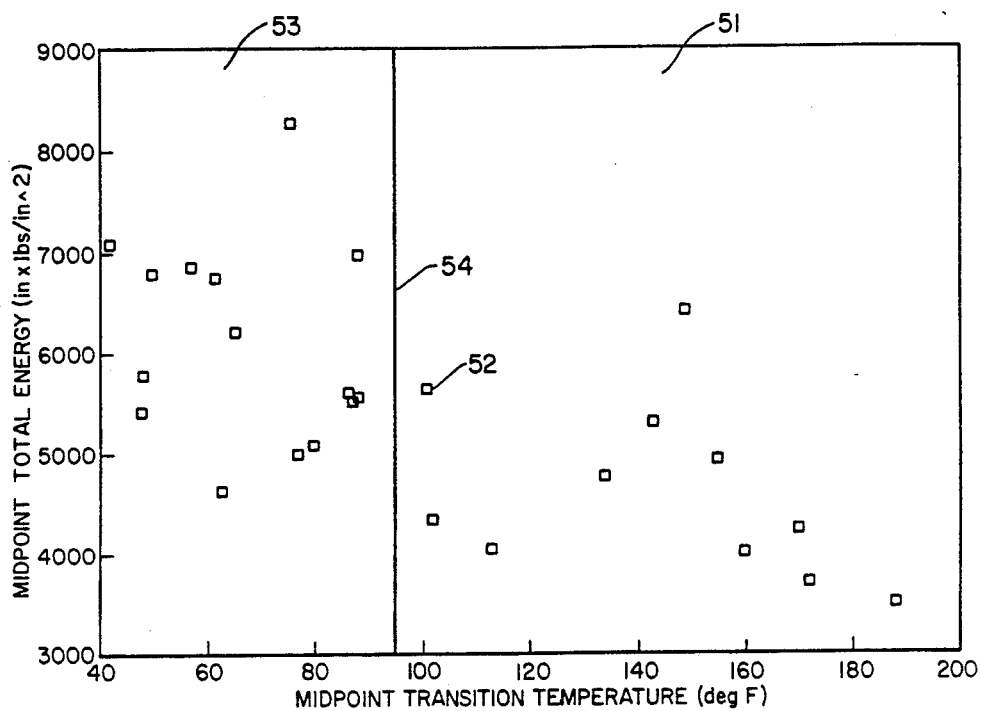
FIG. 10 illustrates the midpoint total energy plotted as a function of the midpoint transition temperature.

A better estimate of the standard maximum midpoint temperature, can be found in FIG. 10. FIG. 10 is a plot of the midpoint total energies ("A" value in Equation 4) as a function of the corresponding midpoint transition temperatures for seven platform steels and all welding conditions. One such data point is indicated by 52. The steels in region 53, to the left of the vertical line 54 which is at approximately 95° F., have high CTOD values, equal to or larger than 0.25 mm. However, those steels with minimum CTOD values less than 0.1 mm are shown in region 51, to the right of the vertical line 54. Therefore the standard maximum midpoint temperature for these platform steels is within 90° F. to 100° F., or approximately 95° F.

Figure 11:
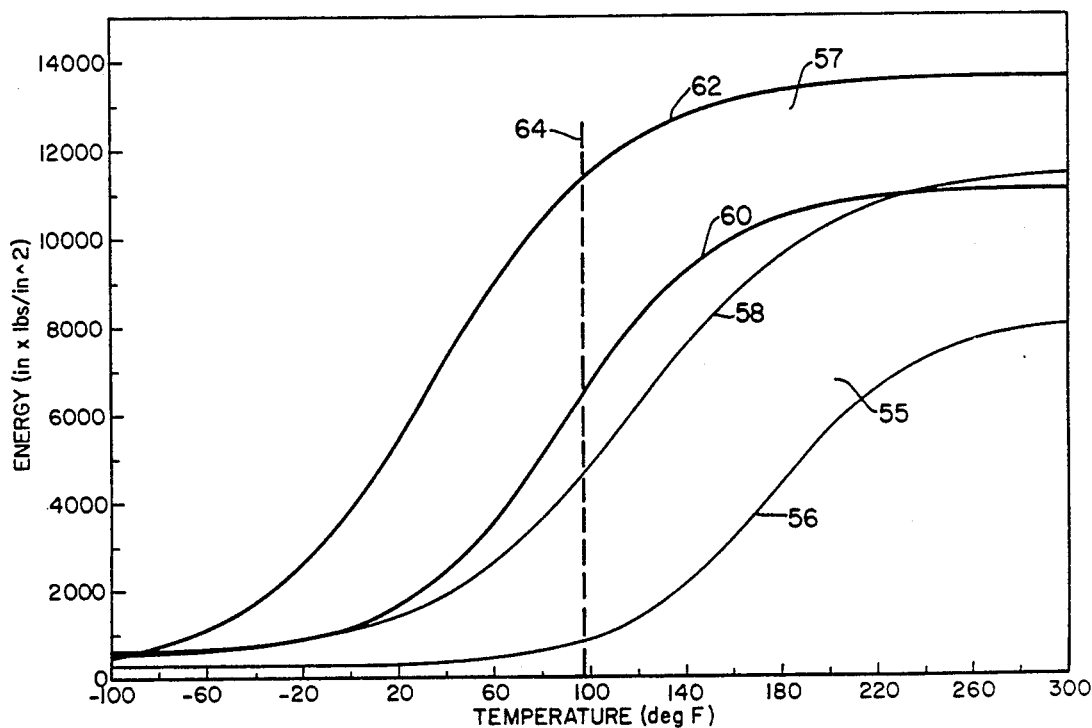
FIG. 11 illustrates the total energy plotted as a function of temperature for several steels at various weld heat input values.

Another acceptable technique for evaluating the relative HAZ toughness of steel is to first plot four previously determined standard total fracture energy curves, as shown in FIG. 11. The total fracture energy curves are generated, for a range of steels using the method previously described. The total fracture energy curves (i.e. total fracture energy plotted as a function of temperature) are determined for each steel at weld heat input values of 3, 5, 3/3, and 5/5 kJ/mm.

The total fracture energy curve having the highest midpoint transition temperature of all of the curves for steels having CTOD values less than 0.10 mm is plotted. Such a curve is illustrated in FIG. 11 as curve 56. The total fracture energy curve having the having CTOD values less than 0.10 mm is also plotted on the same graph. Such a curve is illustrated in FIG. 11 as curve 58. If a total fracture energy curve for a steel falls within curves 56 and 58, that steel may have low CTOD values, as indicated by 55, and thus low HAZ toughness.

The total fracture energy curve having the lowest midpoint transition temperature of all of the curves for steels having CTOD values greater than 0.25 mm is also plotted on the same graph. Such a curve is illustrated in FIG. 11 as curve 62. The total fracture energy curve having the highest midpoint transition temperature of all of the curves for steels having CTOD values greater than 0.25 mm is also plotted on the same graph. Such a curve is illustrated in FIG. 11 as curve 60. If a total fracture energy curve for a steel falls within curves 60 and 62, that steel may have high CTOD values as indicated by 57, and thus high HAZ toughness.

Note that in FIG. 11 curves 60 and 58 have approximately the same upper and lower shelves. These two standard curves have midpoint transition temperatures, respectively, of approximately 90° F. and 100° F. Therefore, the standard maximum midpoint temperature is approximately equal to 95° F. ±5° F., as illustrated in FIG. 11 as dashed line 64. This same analysis could be used with plots of the other fracture properties as a function of temperature.

The present method for determining the HAZ toughness of steel takes around six weeks to complete and can substantially reduce cost. Accordingly, the present invention satisfies the need for a practical method for determining the relative HAZ toughness of steel. It should be understood that the invention is not to be unduly limited to the foregoing which has been set forth for illustrative purposes. Various modifications and alterations of the invention will be apparent to those skilled in the art without departing from the true scope of the invention, as defined in the claims following Appendix A.

APPENDIX A

I. Derivation of Equation 1 (Eq. 6A) of this Appendix)

When the tup of the falling drop weight impacts a sample, the energy, E(t), delivered to the sample will be time-dependent. To calculate the energy, the force, F(t), measured on the tup is used. From Newton's third law, the force measured on the tup will be equal in magnitude, but opposite in sign to the force experienced by the sample. To calculate the energy delivered by the falling weight, the definition of energy is used.

$$E(x) = \int F(x)\, dx \qquad \text{Eq. (1)}$$

where x is the displacement of the sample. To convert displacement into time, the instantaneous velocity, V(t), of the tup must be known:

$$E(t) = \int F(t) V(t) \, dt \qquad \text{Eq. (2a)}$$

where $$V(t) = dx/dt \qquad \text{Eq. (2b)}$$

Since the tup velocity is not measured as a function of time, Newton's first law of motion must be solved to determine the tup velocity:

$$M \, d^2x/dt^2 = Mg - F(t) \qquad \text{Eq. (3)}$$

where M is the mass of the falling weight, and g is the acceleration due to gravity.

Equation 3 has the solution:

$$V(t) = V_o + gt - \frac{1}{M} \int_0^t F(t) dt \qquad \text{Eq. (4)}$$

where $V_o$ is the initial impact velocity. Combining Equation 4 and Equation 2a, $$E(t) = \qquad \text{Eq. (5)}$$

$$V_o \int_0^t F(t) dt + g \int_0^t t F(t) dt - \frac{1}{M} \int_0^t F(t) \int_0^t F(t) dt \, dt$$

Using integration by parts, Equation 5 can be simplified to:

$$E(t) = V_o I_o(t) + g I_1(t) - I_o^2(t)/2M \qquad \text{Eq. (6a)}$$

where $$I_o = \int_0^t F(t) dt = \text{impulse} \qquad \text{Eq. (6b)}$$

and $$I_1 = \int_0^t t F(t) dt = \text{first moment of impulse} \qquad \text{Eq. (6c)}$$

The tup velocity and sample displacement can also be calculated:

$$V(t) = V_o + gt - I_o(t)/M \qquad \text{Eq. (7)}$$

$$x(t) = V_o t + 1/2 g t^2 - I_o(t) t/M + I_1(t)/M \qquad \text{Eq. (8)}$$

Equations 6a-c, 7, and 8 are exact, with no approximations.

II. Derivation of the Equation Used to Determine Dynamic Fracture Toughness (Equation 15 of this Appendix)

Equation 6 calculates the total energy delivered to the sample. Most of this energy is absorbed by the sample to produce a fracture; however, some of this energy is wasted, since the sample transmits this energy into the anvil, or it is absorbed by the tup. The energy absorbed by the machine, $E_m$, must be subtracted from Equation 6 to determine the energy, $E_s$, absorbed by the sample.

$$E_s = E - E_m \qquad \text{Eq. (9)}$$

where:

$$E_m = P^2 m [C_T - C_{ND}/12YB]/2 \qquad \text{Eq. (10)}$$

where
$P_m$ = maximum or peak load.
$C_T$ = total system compliance (ft/lb).
Y = Youngs' Modulus for sample = $30 \times 10^6$ psi.
B = sample thickness = 0.394 in.
$C_{ND}$ = dimensionless sample compliance = 56.75 for crack depth, a/w = 0.5.

The total system compliance can be calculated from the dynamic-load data:

$$C_T = t_1(V_o/P_1 - gt_1/4W) \qquad \text{Eq. (11a)}$$

where $P_1$ is the load at general yielding of the sample, and $t_1$ is the time for general yielding to occur. The first term is always much greater than the second term. Consequently, a good approximation is $$C_T = t_1 V_o/P_1 \qquad \text{Eq. (11b)}$$

For a constant crack depth, the sample compliance will be constant.

$$C_{ND}/12YB = 4.00 \times 10^{-7} \, ft/lb$$

The J integral, $J_{int}$, and yield stress $\sigma_y$, can also be calculated:

$$J_{int} = 12 E_{ic} F(a/w)/bB \qquad \text{Eq. (12)}$$

$$\sigma_y = 2.85 \times 10^{-3} P_1 W/Bb^2 \qquad \text{Eq. (13)}$$

where $E_{ic}$ is the corrected initiation energy, B is the sample width, and b = (W − a) is the uncracked ligament width. The flow stress, $\sigma_f$, and dynamic fracture toughness, $K_{Id}$, can also be calculated as $$\sigma_f = 2.85 \times 10^{-3}(P_1 + P_m)W/2Bb^2 \qquad \text{Eq. (14)}$$

$$K_{Id} = [Y J_{int}]^{1/2}/1000 \qquad \text{Eq. (15)}$$

where the test conditions b and a $> 25 \, J_{int}/\sigma_f$ should apply for Equation 15.

III. Derivation of Equation 4 (Equation 16 in the Appendix)

If the velocity of the falling drop weight, $V_o$, at the moment of impact and the velocity $V_1$, after breaking the sample, the law for the conservation of energy can be used to calculate the energy absorbed during impact:

$$E = M(V_o^2 - V_1^2)/2 + MgX_d \qquad \text{Eq. (16)}$$

where $X_d$ is the distance between the photodetectors, and the acceleration of gravity g = 32.1291 ft/sec$^2$ The accuracy of the energy, &E, calculated in Equation 16 is estimated to be $$\&E = M(V_o - V_1)V_o(\&V/V_o) \qquad \text{Eq. (17)}$$

where $\&V/V_o$ is the accuracy of the velocity measurements. The accuracy of the velocity measurement is limited to only the uncertainty in the IR photodetector beam width, which was calibrated within ±1 percent. Therefore, the photodetectors can determine the energy to within ±0.4 ft-lb.

What we claim is:

1. A method for determining the relative heat affected zone ("HAZ") toughness of steel prior to welding said steel at desired welding conditions; said welding conditions include weld heat input, peak temperature, preheat, and steel thickness; said HAZ having coarse-grain regions resulting from multipass welding of said steel at said desired welding conditions; said steel having thermal cycles corresponding to each of said coarse-grain regions and fracture properties necessary to fracture said steel; said fracture properties selected from the group consisting of total fracture energy, initiation energy, propagation energy, and dynamic fracture toughness; said steel being within a range of steels having a previously determined standard maximum midpoint transition temperature and minimum crack tip opening displacement ("CTOD") values; said method comprising the steps of:

(a) determining the thermal cycles at the desired welding conditions corresponding to at least two of said coarse-grain regions of said HAZ;

(b) heating and cooling said steel in accordance with said thermal cycles determined in step (a) to simulate said HAZ, including said coarse-grain regions;

(c) fracturing said steel at a plurality of test temperatures;

(d) determining the value of the same fracture property for each of said fracture test temperatures;

(e) plotting said fracture property values determined in step (d) as a function of fracture test temperature;

(f) determining the midpoint transition temperature from said plot; and (e) comparing said midpoint transition temperature to said standard maximum midpoint transition temperature; whereby if said midpoint transition temperature is greater than said standard maximum midpoint transition temperature, said steel may have a low toughness, but if said midpoint transaction temperature is less than said standard maximum midpoint transition temperature, said steel may have a high toughness.

2. The method of claim 1 wherein said thermal cycles are determined using thermocouples placed in said steel.

3. The method of claim 1 wherein said desired welding conditions comprise said weld heat input values of approximately 1.5 to 5 kJ/mm, said peak temperature between 1200° C. and 1400° C., said preheat temperature of approximately 93° C., and steel thickness of approximately 2 inches or greater.

4. The method of claim 1 wherein said steel is heated and cooled using a weld thermal cycle simulator.

5. The method of claim 1 wherein step (c) further comprises the steps of:

(c1) machining said steel to obtain at least 12 Charpy size samples, each having dimensions of approximately 10 mm ×10 mm ×55 mm;

(c2) machining a notch in each of said steel samples of approximately 0.005 inches;

(c3) producing a fatigue precrack of approximately 5 mm in each of said steel samples; and (c4) fracturing each of said precracked steel samples for a plurality of test temperatures ranging from approximately −150° F. to 300° F.

6. The method of claim 5 wherein step (c4) is performed using Instrumental Precracked Charpy ("IPC") equipment.

7. The method of claim 1 wherein the test temperatures referred to in step (c) range from approximately −150° F. to 300° F.

8. The method of claim 1 wherein the fracture property referred to in step (d) comprises said total fracture energy, said initiation energy, said propagation energy, or said dynamic fracture toughness.

9. The method of claim 1 wherein the previously determined standard maximum midpoint transition temperature for said range of steels is determined by the method comprising the steps of:

(a) determining for each of said steels in said range of steels the thermal cycles, at the desired welding conditions, corresponding to at least two of said coarse-grain regions of said HAZ;

(b) heating and cooling each of said steels in said range of steels in accordance with said thermal cycles determined in step (a) to simulate said HAZ, including said coarse-grain regions;

(c) fracturing each of said steels in said range of steels at a plurality of test temperatures;

(d) determining for each of said steels in said range of steels the value of the same fracture property for each of said test temperatures;

(e) plotting said fracture property values determined in step (d) for each of said steels in said range of steels as a function of fracture test temperature;

(f) determining the midpoint transition temperature for each of said steels in said range of steels from said plots; and (e) correlating said midpoint transition temperatures of each of said steels with the previously determined CTOD values for each of said steels, thereby deriving said standard maximum midpoint transition temperature for said range of steels.

10. The method of claim 1 wherein said range of steels have a specified minimum yield strength of approximately 50 ksi, a typical tensile strength of approximately 2 to 3.5 inches, and a standard maximum midpoint transition temperature for said range of approximately 95° F.

11. The method of claim 1 wherein one of said coarse-grain regions of said HAZ is the single thermal cycle region ("CGHAZ") and the other of said coarse-grain regions of said HAZ is the two-thermal-cycle intercritically reheated region ("IRCG").

* * * * *